(12) United States Patent
Schabbach et al.

(10) Patent No.: US 10,369,279 B2
(45) Date of Patent: Aug. 6, 2019

(54) DRIVE MECHANISM FOR A NEEDLE INSERTION ARRANGEMENT

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 72 days.

(21) Appl. No.: 14/916,694

(22) PCT Filed: Sep. 2, 2014

(86) PCT No.: PCT/EP2014/068599
§ 371 (c)(1),
(2) Date: Mar. 4, 2016

(87) PCT Pub. No.: WO2015/032745
PCT Pub. Date: Mar. 12, 2015

(65) Prior Publication Data
US 2016/0213840 A1  Jul. 28, 2016

(30) Foreign Application Priority Data
Sep. 5, 2013 (EP) .................................... 13183154

(51) Int. Cl.
*A61M 5/158* (2006.01)
*A61M 5/32* (2006.01)
*A61M 5/46* (2006.01)

(52) U.S. Cl.
CPC .......... *A61M 5/158* (2013.01); *A61M 5/3287* (2013.01); *A61M 5/46* (2013.01);
(Continued)

(58) Field of Classification Search
CPC ...... A61M 5/158; A61M 5/3287; A61M 5/46; A61M 2005/1581; A61M 2005/1583;
(Continued)

(56) References Cited
U.S. PATENT DOCUMENTS 3,521,676 A  7/1970  MacIssac
6,599,272 B1 *  7/2003  Hjertman .............. A61M 5/315
604/197
(Continued)

FOREIGN PATENT DOCUMENTS

DE  1907569  5/1959
GB  813439  10/1969
(Continued)

OTHER PUBLICATIONS

International Search Report and Written Opinion in International Application No. PCT/EP2014/068599, dated Oct. 27, 2014, 8 pages.
(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

The invention relates to a drive mechanism (9) for a needle insertion arrangement (1), the drive mechanism (9) including:—a cross beam (16) linearly movable in a distal direction (D) and a proximal direction (P) for moving an injection needle (2),—an actuator (5),—a slider (12) coupled to the actuator (5) and linearly movable in a transversal direction (T) at right angles relative the distal direction D and the proximal direction D,—a cam (14) on one of the cross beam (16) and the slider (12),—a guide track (13) in the other one of the cross beam (16) and the slider (12) adapted to engage the cam (14), the guide track including a sloped section (13.3) such that the cross beam (16) is moved on movement of the slider (12).

18 Claims, 5 Drawing Sheets

(52) U.S. Cl.
CPC .............. *A61M 2005/1583* (2013.01); *A61M 2005/1585* (2013.01)

(58) Field of Classification Search
CPC .... A61M 2005/1585; A61M 2005/206; A61B 2017/00398
See application file for complete search history.

(56) References Cited

U.S. PATENT DOCUMENTS

| | | | |
|---|---|---|---|
| 6,960,192 B1 | 11/2005 | Flaherty et al. | |
| 2003/0171716 A1 | 9/2003 | Ejlersen | |
| 2007/0072317 A1 | 3/2007 | Hwang et al. | |
| 2008/0269687 A1* | 10/2008 | Chong | A61L 15/58 604/180 |
| 2009/0062815 A1* | 3/2009 | Karasiuk | A45D 34/04 606/131 |
| 2017/0266390 A1* | 9/2017 | Baba | A61M 5/31596 |

FOREIGN PATENT DOCUMENTS

| | | |
|---|---|---|
| JP | H8-1996-502180 | 3/1996 |
| JP | 2005-518253 | 6/2005 |
| JP | 2005-526560 | 9/2005 |
| JP | 2010-517700 | 5/2010 |
| WO | WO03/072172 | 9/2003 |
| WO | WO 2008/098246 | 8/2008 |
| WO | WO2009/024522 | 2/2009 |

OTHER PUBLICATIONS

International Preliminary Report on Patentability in International Application No. PCT/EP2014/068599, dated Mar. 8, 2016, 6 pages.
Rote Liste, "50. Hypophysen-, Hypothalamushormone, andere regulatorische Peptide u. ihre Hemmstoffe," Chapter 50, ed. 2008, 20 pages.

* cited by examiner

DRIVE MECHANISM FOR A NEEDLE INSERTION ARRANGEMENT

CROSS-REFERENCE TO RELATED APPLICATIONS

This application is a U.S. national stage application under 35 USC § 371 of International Application No. PCT/EP2014/068599, filed on Sep. 2, 2014, which claims priority to European Patent Application No. 13183154.7, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

There remains a need for an improved drive mechanism for a needle insertion arrangement.

SUMMARY OF THE INVENTION

Aspects of the present invention can provide an improved drive mechanism for a needle insertion arrangement.

The aspects can be implemented by a drive mechanism for a needle insertion arrangement according to claim 1.

Exemplary embodiments of the invention are given in the dependent claims.

According to the invention a drive mechanism for a needle insertion arrangement comprises
  a cross beam linearly movable in a distal direction and a proximal direction for moving an injection needle,
  an actuator,
  a slider coupled to the actuator and linearly movable in a transversal direction at right angles relative the distal direction and the proximal direction,
  a cam on one of the cross beam and the slider,
  a guide track in the other one of the cross beam and the slider adapted to engage the cam, the guide track comprising a sloped section such that the cross beam is moved on movement of the slider.

When the drive mechanism is applied in a needle insertion arrangement it allows for limited space requirements thus allowing for low profile injection devices with a high wearing comfort. The drive mechanism achieves high speed needle movements and exact needle guidance thus reducing pain for the patients when inserting and retracting the needle and increasing consumer acceptance and satisfaction. The low part count of the drive mechanism and the low requirements for electronic equipment allow for an increased mechanical robustness and low manufacturing costs. The drive mechanism is a fault-tolerant system. The movement of the needle may be customized to the respective application by modifying a gear transmission ratio of the rack and pinion gear, e.g. by selecting the size of the pinion and by varying the slope of the guide track. In an exemplary embodiment the actuator may be replaced by a handle for manually operating the drive mechanism. The drive mechanism is permanently positively coupled to the needle. When using a sensor for detecting whether the needle is in the extended position, this allows for ensuring that an injection is only performed when the needle is in the extended position, e.g. inserted in an injection site at insertion depth.

In an exemplary embodiment a needle retainer is adapted to retain an injection needle, the needle retainer arranged to be moved between a retracted position and an extended position, wherein the needle retainer is adapted to be moved by the cross beam.

In an exemplary embodiment the needle retainer is integrated with the cross beam.

In an exemplary embodiment the guide track further comprises:
  a proximal transversal section aligned in the transversal direction,
  a distal transversal section aligned in the transversal direction and offset relative the proximal transversal section in the distal direction and in the transversal direction, wherein the sloped section connects the proximal transversal section with the distal transversal section.

In an exemplary embodiment the guide track comprises a sigmoid shape.

In an exemplary embodiment the guide track is arranged as a notch milled into the slider or into the cross beam.

In an exemplary embodiment the actuator is arranged as a linear actuator coupled to the slider.

In an exemplary embodiment the actuator is arranged as an electrical motor coupled to a pinion engaged to a rack arranged on or coupled to the slider.

In an exemplary embodiment at least one linear guide is arranged for guiding the needle retainer and/or the cross beam.

The drive mechanism may be applied in an insertion arrangement for moving an injection needle between a retracted position and an extended position, comprising a disposable unit, comprising a needle base, to which the needle is fixed, wherein the needle retainer is adapted to retain the needle base.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
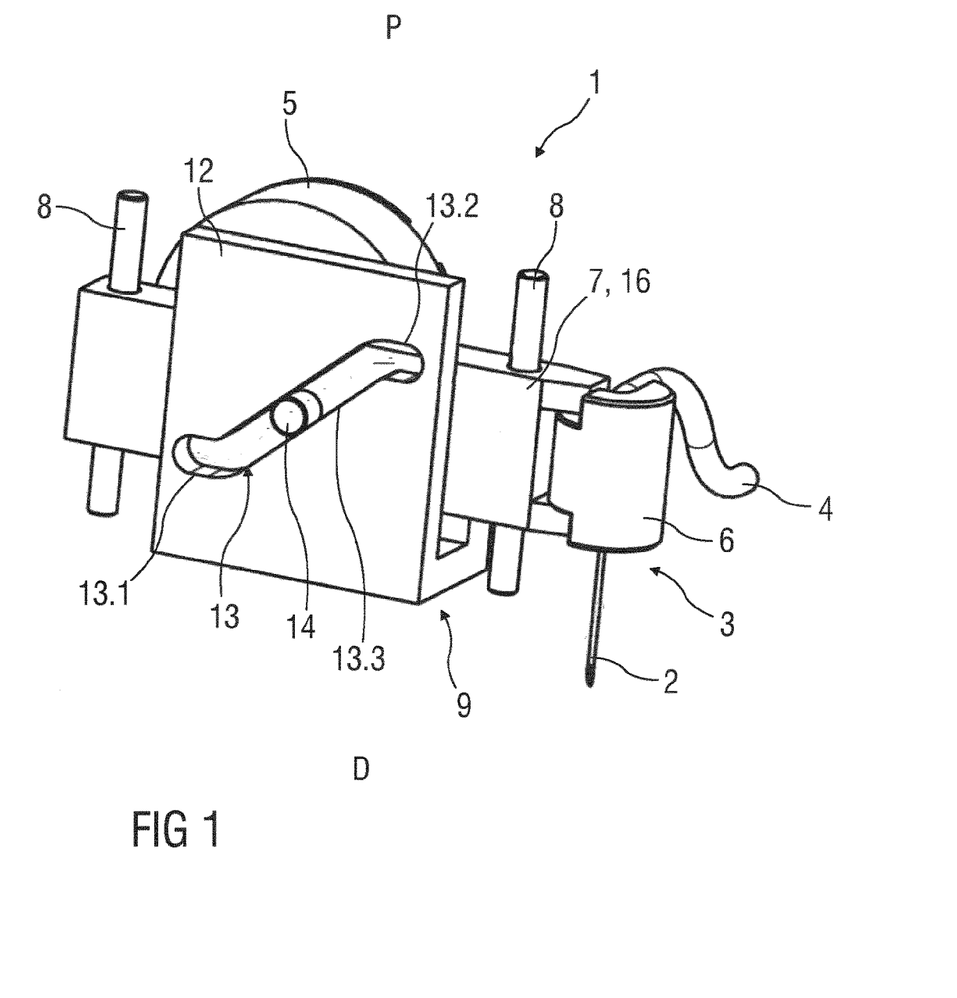
FIG. 1 is a schematic perspective view of an exemplary embodiment of an insertion arrangement for inserting and retracting an injection needle.
Figure 2:
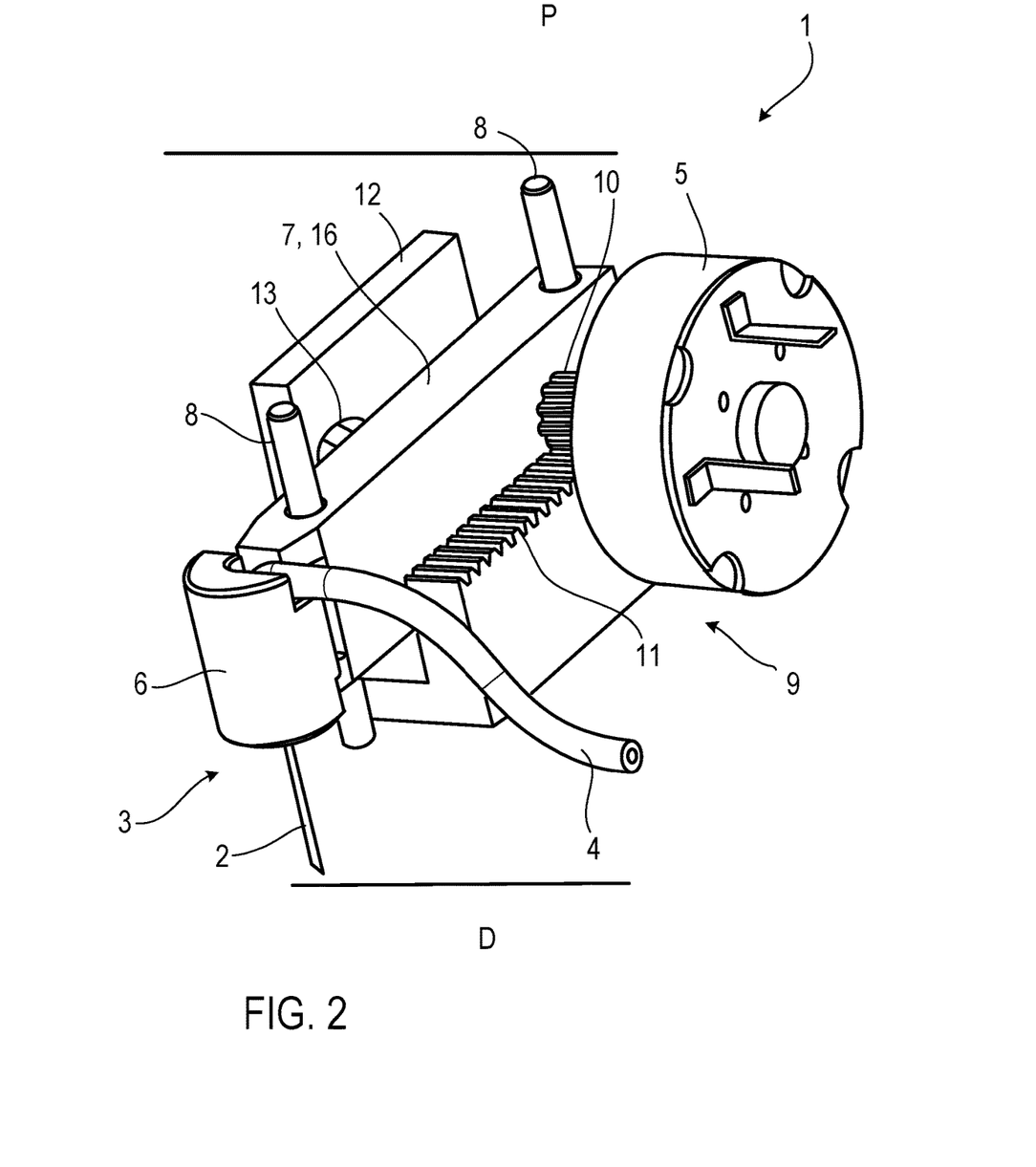
FIG. 2 is another schematic perspective view of the insertion arrangement.

FIG. 1 is a schematic perspective view of an exemplary embodiment of an insertion arrangement 1 for automatically or semi-automatically inserting an injection needle 2 into an injection site. FIG. 2 is another related schematic perspective view. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a forked needle retainer 7 which is arranged to be moved in a distal direction D and/or a proximal direction P along two linear guides 8 arranged in parallel. This linear movement corresponds to insertion of the needle 2 into the injection site, e.g. subcutaneous body tissue and removal from the injection site, respectively.

The drive mechanism 9 for the needle 2 comprises an actuator 5, e.g. an electrical motor driving a pinion 10 engaged to a rack 11 arranged on or coupled to a slider 12. The slider 12 is arranged to be linearly moved in a transversal direction T at right angles relative the distal direction D and the proximal direction D, only. Respective guides may be arranged (not illustrated) for preventing other movements of the slider 12. The slider 12 comprises a guide track 13 with a curved geometry adapted to be engaged by a cam 14 on the needle retainer 7 serving as a cross beam 16. The guide track 13 comprises:

a proximal transversal section 13.1 aligned in the transversal direction T, a distal transversal section 13.2 aligned in the transversal direction T and offset relative the proximal transversal section 13.1 in the distal direction D and in the transversal direction T, a sloped section 13.3 arranged at an angle with respect to the transversal direction T and connecting the proximal transversal section 13.1 with the distal transversal section 13.2.

In the illustrated embodiment the guide track 13 is arranged as a notch milled into the slider 12.

If the slider 12 is moved in the transversal direction T by rotating the actuator 5, the guide track 13 slides along the cam 14 thus moving the needle retainer 7 and the needle 2 in the distal direction D or the proximal direction P depending on a rotational direction of the actuator 5.

Figure 3:
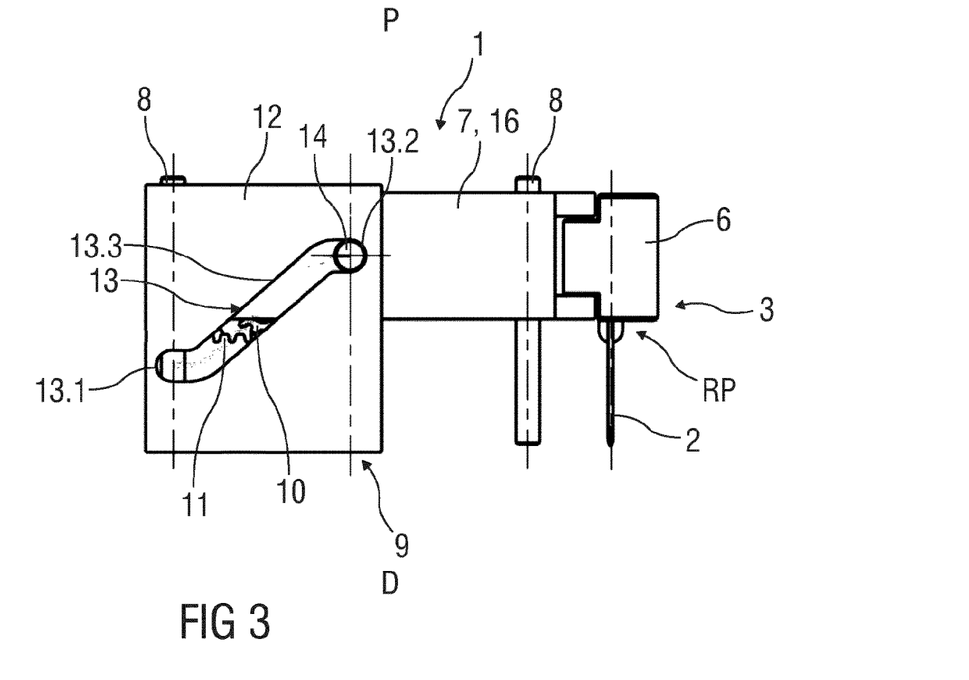
FIG. 3 is a schematic side view of the insertion arrangement in an initial position, wherein the needle is in a retracted position.

A sequence of operation of the insertion arrangement 1 is as follows:

FIG. 3 is a schematic side view of the insertion arrangement 1 in an initial position. The disposable unit 3 with the needle base 6, the needle 2 and the tube 4 has been inserted in the forked needle retainer 7. The needle retainer 7 and the needle 2 are in a retracted position RP. The cam 14 is located in the proximal transversal section 13.1 of the guide track 13. The actuator 5 and the pinion 10 start rotating in a first rotational direction R1, thus translating the rack 11 and the slider 12 in a first transversal direction T1 towards the needle 2. As long as the cam 14 is located in the proximal transversal section 13.1 during that movement the needle retainer 7 remains in position while the actuator approaches its nominal rotational speed.

Figure 4:
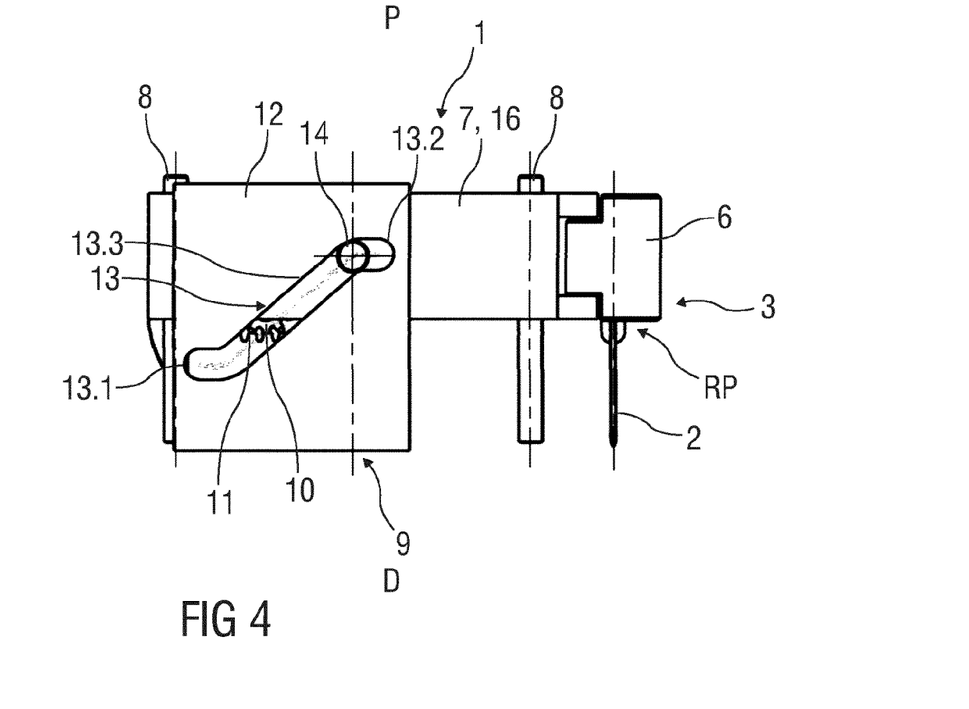
FIG. 4 is a schematic side view of the insertion arrangement with a cam on a needle retainer entering a sloped section of a guide track.

FIG. 4 is a schematic side view of the insertion arrangement 1 with the cam 14 entering the sloped section 13.3. The actuator 5 rotates at nominal rotational speed. As the cam 14 enters the sloped section 13.3 the needle retainer 7 and the needle start moving in the distal direction D.

Figure 5:
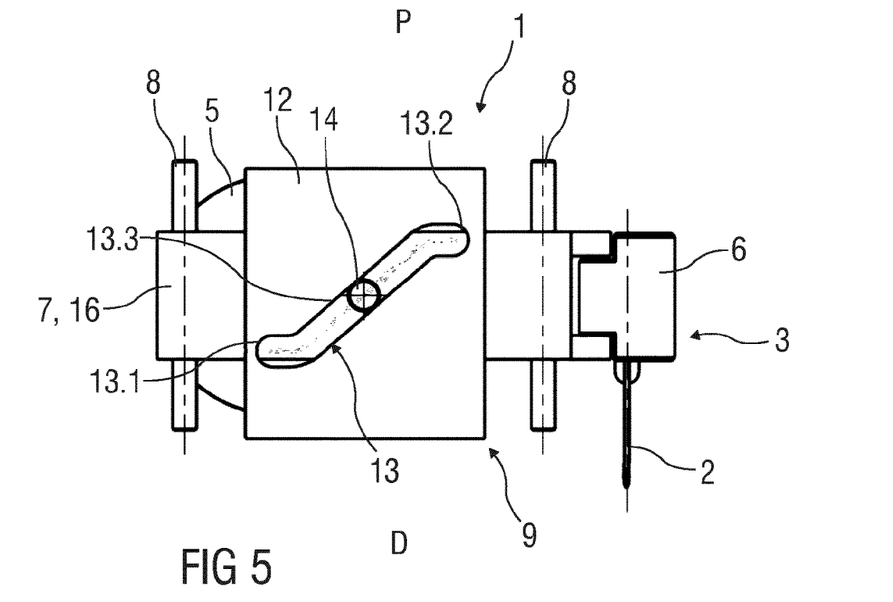
FIG. 5 is a schematic side view of the insertion arrangement with the cam located in the sloped section.

FIG. 5 is a schematic side view of the insertion arrangement 1 with the cam 14 located in the sloped section 13.3. The actuator 5 continues rotating at nominal rotational speed. As the cam 14 slides along the sloped section 13.3 the needle retainer 7 and the needle continue moving in the distal direction D with a speed determined by the nominal rotational speed of the actuator 5 and by the slope of the sloped section 13.3.

Figure 6:
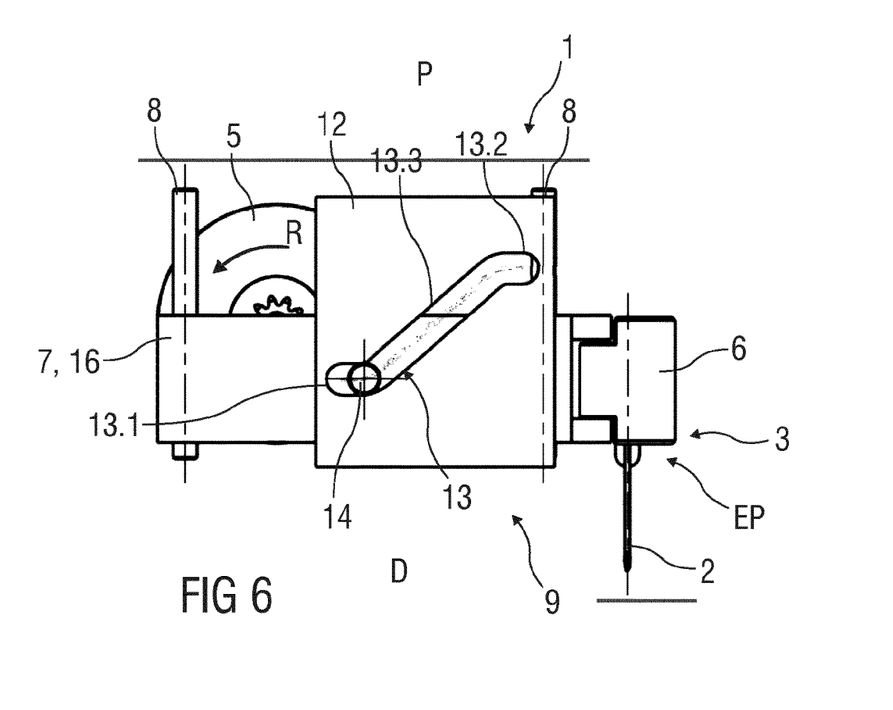
FIG. 6 is a schematic side view of the insertion arrangement with the cam entering a distal transversal section of the guide track, wherein the needle is in an extended position.

FIG. 6 is a schematic side view of the insertion arrangement 1 with the cam 14 entering the distal transversal section 13.2. The actuator 5 continues rotating at nominal rotational speed. As the cam 14 reaches the distal transversal section 13.2 the slope of the guide track 13 is reduced to zero such that the needle retainer 7 and the needle 2 arrive in an extended position EP and stop moving. In the extended position EP the needle 2 has reached its insertion depth in the injection site, e.g. in the subcutaneous body tissue.

Figure 7:
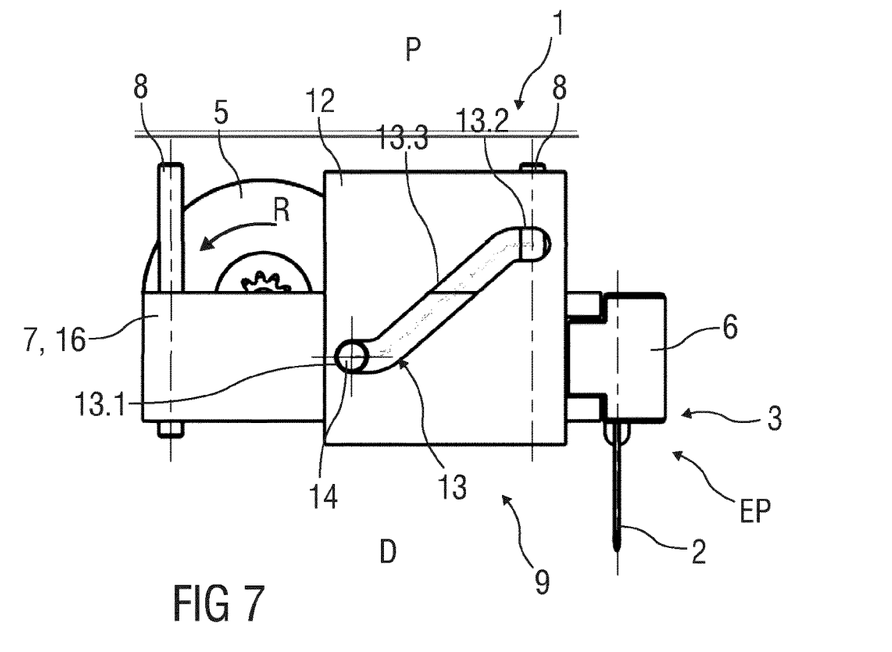
FIG. 7 is a schematic side view of the insertion arrangement with the cam moving within the distal transversal section.

FIG. 7 is a schematic side view of the insertion arrangement 1 with the cam 14 moving within the distal transversal section 13.2. The actuator 5 runs out until coming to a standstill thus also ending the movement of the rack 11 and the slider 12. A sensor for detecting that the needle 2 is in the extended position EP may be used to shut off the actuator 5.

Subsequently, the needle 2 may be retracted into the retracted position RP in an analogous manner by reversing the rotational direction of the actuator 5.

The characteristics of the movement of the needle retainer 7 and the needle 2 may be varied by altering the geometry of the guide track 13. In the illustrated embodiment the proximal transversal section 13.1 and the distal transversal section 13.2 allow for starting the actuator 5 up and running it out, in particular if the actuator 5 is an electrical motor. The sloped section 13.3 allows for a rapid extension and retraction of the needle 2 in order to insert it into an injection site, e.g. subcutaneous body tissue or to remove it therefrom. In an alternative embodiment the geometry of the guide track 13 may be modified to achieve a slower start of the needle extension for piercing the injection site and a consecutive fast continuation of the needle extension for approaching the insertion depth and a final slow stop of the needle extension, e.g. by a sigmoid shape of the guide track 13.

In an alternative embodiment the cam 14 could be arranged on a cross beam adapted to engage the separate needle retainer 7. In the illustrated embodiment the needle retainer 7 serves as a cross beam 16.

In an alternative embodiment the guide track 13 could be arranged in the cross beam 16 or the needle retainer 7 while the cam would be arranged on the slider 12.

In an alternative embodiment the slider 12 could be moved by a linear actuator such that the rack and pinion gear would not be required.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ψ-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-N H2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 insertion arrangement
2 injection needle
3 disposable unit
4 tube
5 actuator 6 needle base
7 needle retainer
8 linear guide
9 drive mechanism
10 pinion
11 rack
12 slider
13 guide track
13.1 proximal transversal section
13.2 distal transversal section
13.3 sloped section
14 cam
16 cross beam
D distal direction
EP extended position
P proximal direction
R1 first rotational direction
R2 second rotational direction
RP retracted position
T transversal direction

The invention claimed is:

1. A drive mechanism for a needle insertion arrangement of an injection device, the drive mechanism comprising:
   a cross beam linearly movable in a distal direction and a proximal direction for moving an injection needle;
   an actuator;
   a slider coupled to the actuator and linearly movable in a transversal direction at right angles relative the distal direction and the proximal direction;
   a cam extending from the cross beam or the slider; and
   a guide track in the cross beam or the slider that the cam does not extend from, the guide track adapted to engage the cam, the guide track comprising a sloped section such that the cross beam is moved on movement of the slider, wherein the cam has a first position on the sloped section and a second position on the sloped section such that, as the cam moves from the first position to the second position, the needle moves from a retracted position to an extended position; and wherein the entire sloped section is arranged at a first angle with respect to the transversal direction.

2. The drive mechanism according to claim 1, comprising a needle retainer adapted to retain an injection needle, the needle retainer arranged to be moved between a retracted position and an extended position, wherein the needle retainer is adapted to be moved by the cross beam.

3. The drive mechanism according to claim 2, wherein at least one linear guide is arranged for guiding the needle retainer or the cross beam.

4. The drive mechanism according to claim 2, wherein the needle retainer is integrated with the cross beam.

5. The drive mechanism according to claim 1, wherein the guide track further comprises:
   a proximal transversal section aligned in the transversal direction;
   a distal transversal section aligned in the transversal direction and offset relative the proximal transversal section in the distal direction and in the transversal direction, wherein the sloped section connects the proximal transversal section with the distal transversal section.

6. The drive mechanism according to claim 1, wherein the guide track comprises a sigmoid shape.

7. The drive mechanism according to claim 1, wherein the guide track comprises a notch milled into the slider or into the cross beam.

8. The drive mechanism according to claim 1, wherein the actuator comprises a linear actuator coupled to the slider.

9. The drive mechanism according to claim 1, wherein the actuator comprises an electrical motor coupled to a pinion engaged to a rack arranged on or coupled to the slider.

10. An insertion arrangement for moving an injection needle between a retracted position and an extended position, the insertion arrangement comprising:
    a disposable unit comprising a needle base to which the needle is fixed; and
    a drive mechanism comprising:
      a cross beam linearly movable in a distal direction and a proximal direction for moving an injection needle;
      an actuator;
      a slider coupled to the actuator and linearly movable in a transversal direction at right angles relative the distal direction and the proximal direction;
      a cam extending from the cross beam or the slider; and
      a guide track in the cross beam or the slider that the cam does not extend from, the guide track adapted to engage the cam, the guide track comprising a sloped section such that the cross beam is moved on movement of the slider, wherein the cam has a first position on the sloped section and a second position on the sloped section such that, as the cam moves from the first position to the second position, the needle moves from a retracted position to an extended position, and wherein the entire sloped section is arranged at a first angle with respect to the transversal direction,
    wherein a needle retainer is adapted to retain the needle base.

11. The insertion arrangement according to claim 10, comprising the needle retainer, the needle retainer arranged to be moved between a retracted position and an extended position, wherein the needle retainer is adapted to be moved by the cross beam.

12. The insertion arrangement according to claim 11, wherein at least one linear guide is arranged for guiding the needle retainer or the cross beam.

13. The insertion arrangement according to claim 11, wherein the needle retainer is integrated with the cross beam.

14. The insertion arrangement according to claim 10, wherein the guide track further comprises:
    a proximal transversal section aligned in the transversal direction;
    a distal transversal section aligned in the transversal direction and offset relative the proximal transversal section in the distal direction and in the transversal direction, wherein the sloped section connects the proximal transversal section with the distal transversal section.

15. The insertion arrangement according to claim 10, wherein the guide track comprises a sigmoid shape.

16. The insertion arrangement according to claim 10, wherein the guide track comprises a notch milled into the slider or into the cross beam.

17. The insertion arrangement according to claim 10, wherein the actuator comprises a linear actuator coupled to the slider.

18. An auto-injector comprising:
    an insertion arrangement for moving an injection needle between a retracted position and an extended position, the insertion arrangement comprising:
      a disposable unit comprising a needle base to which the needle is fixed;

a drive mechanism comprising:
- a cross beam linearly movable in a distal direction and a proximal direction for moving an injection needle;
- an actuator;
- a slider coupled to the actuator and linearly movable in a transversal direction at right angles relative the distal direction and the proximal direction;
- a cam extending from the cross beam or the slider; and
- a guide track in the cross beam or the slider that the cam does not extend from, the guide track adapted to engage the cam, the guide track comprising a sloped section such that the cross beam is moved on movement of the slider, wherein the cam has a first position on the sloped section and a second position on the sloped section such that, as the cam moves from the first position to the second position, the needle moves from a retracted position to an extended position, and wherein the entire sloped section is arranged at a first angle with respect to the transversal direction, wherein a needle retainer is adapted to retain the needle base; and wherein the injection needle is configured to couple with a drug container, the drug container carrying a medicament consisting of at least one pharmaceutically active compound.

\* \* \* \* \*